United States Patent [19]
Schat et al.

[11] Patent Number: 5,965,139
[45] Date of Patent: Oct. 12, 1999

[54] CHICKEN INFECTIOUS ANEMIA VIRUS VACCINE

[75] Inventors: Karel A. Schat, Ithaca, N.Y.; Christiane Soine, Heidelberg, Germany; Benjamin Lucio; Randy Renshaw, both of Ithaca, N.Y.

[73] Assignee: Cornell Research Foundation, Inc., Ithaca, N.Y.

[21] Appl. No.: 09/061,304

[22] Filed: Apr. 16, 1998

Related U.S. Application Data

[60] Division of application No. 08/478,086, Jul. 3, 1995, which is a continuation-in-part of application No. 08/271,094, Jul. 6, 1994, abandoned.

[51] Int. Cl.$^6$ .......................... A61K 39/12; C12N 15/34; C12N 7/01; C12N 5/10
[52] U.S. Cl. ..................... 424/199.1; 424/185.1; 424/186.1; 424/192.1; 424/193.1; 424/196.11; 424/202.1; 424/204.1; 424/214.1; 424/229.1; 424/278.1; 424/816; 435/69.1; 435/69.3; 435/235.1; 435/252.3; 435/254.11; 435/320.1; 536/23.72
[58] Field of Search .............................. 424/185.1, 186.1, 424/192.1, 193.1, 196.11, 199.1, 202.1, 204.1, 214.1, 229.1, 278.1, 816; 435/69.1, 69.3, 235.1, 252.3, 254.11, 320.1; 536/23.72

[56] References Cited

U.S. PATENT DOCUMENTS 5,554,525  9/1996  Sondermaijer et al. ............. 435/240.1

OTHER PUBLICATIONS

Claessens et al., "Molecular Cloning and sequence analysis of the genome of chicken anaemia agent", *Journal of General Virology*, 72, 1991, pp. 2003–2006.

Noteborn et al., "Characterization of Cloned Chicken Anemia Virus DNA That Contains All Elements for the Infectious Replication Cycle", *Journal of General Virology*, 72, 1991, pp. 2003–2006.

Meehan et al., "Characterization of viral DNAs from cells infected with chicken anaemia agent: sequence analysis of the cloned replicative form and transfection capabilities of cloned genome fragments", *Archives of Virology*, 124 (1992) pp. 301–319.

*Primary Examiner*—Laurie Scheiner
*Attorney, Agent, or Firm*—Hodgson, Russ, Andrews, Woods & Goodyear, LLP

[57] ABSTRACT

Novel sequences in the genome of a wild type isolate of chicken infectious anemia virus are described, The amino acid sequence of a polypeptide, VP1, encoded by a novel sequence is also disclosed. Additionally, disclosed are the unexpected properties of the isolate which are related to novel amino acids positioned in the amino acid sequence of this isolate's VP1, as compared to the sequence of VP1 found in cell culture-adapted strains; and use of the novel sequences and their respective polypeptides in strategies to control chicken infectious anemia such as by vaccination.

| | | 60 h | MSB1(L)[1] | | | 6 d | MSB1(S)[2] | |
|---|---|---|---|---|---|---|---|---|
| | | | 9 d | 17 d | 24 d | | 16 d | 25 d |
| CIA-1 | | 0.04 | - | - | - | - | - | - |
| | | 0.03 | - | - | - | - | - | - |
| | | 0.03 | - | - | - | - | 0.07 | 0.10 |
| | | 0.06 | - | - | - | 85.0 | n.d. | n.d. |
| | | 0.04 | 2.70 | n.d. | n.d. | 69.0 | 0.08 | 1.10 |
| Cux-1 | | 0.06 | 2.90 | n.d. | n.d. | 90.0 | n.d. | n.d. |
| | | 0.07 | 0.08 | 3.0 | 33.2 | 46.0 | n.d. | n.d. |
| | | 0.04 | - | - | - | - | 1.80 | 18.5 |
| | | 0.03 | 0.02 | 5.6 | 49.0 | 57.0 | n.d. | n.d. |
| | | 0.06 | | | | | | |

% IFA+ cells

[1] post-transfection
[2] post-transfer

CHICKEN INFECTIOUS ANEMIA VIRUS VACCINE

This application is a divisional of co-pending U.S. patent application Ser. No. 08/478,086, filed Jul. 3, 1995, which is a continuation-in-part of U.S. patent application Ser. No. 08/271,094, filed Jul. 6, 1994, now abandoned, which are herein incorporated by reference.

1. BACKGROUND OF THE INVENTION

1.1 Field of the Invention

The present invention relates to a particular strain (CIA-1) of chicken infectious anemia virus (CIAV) having a polypeptide comprising a novel amino acid sequence which can be used to vaccinate poultry against CIAV. More particularly, the invention relates to a novel, naturally occurring CIAV isolate which has not been adapted to cell culture; and which, due to the novel amino acid sequence of a major viral polypeptide, exhibits a difference in pathogenic potential and cell tropism as compared to cell culture-adapted strains.

1.2 Description of the Background and Related Art

Chicken infectious anemia virus (CIAV) was first isolated in Japan in 1979 during an investigation of a Marek's disease vaccination break (Yuasa et al., 1979, *Avian Dis.* 23: 366–385). Since that time, CIAV has been detected in commercial poultry in all major poultry producing countries (van Bülow et al., 1991, pp.690–699) in *Diseases of Poultry*, 9th edition, Iowa State University Press).

CIAV can cause clinical diseases, characterized by anemia, hemorrhages and immunosuppressive, in young susceptible chickens. Atrophy of the thymus and of the bone marrow are characteristic and consistent lesions of CIAV-infected chickens. Lymphocyte depletion in the thymus, and occasionally in the bursa of Fabricius, results in immunosuppressive and increased susceptibility to secondary viral, bacterial, or fungal infections which then complicate the course of the disease. The immunosuppressive may cause aggravated disease after infection with one or more of Marek's disease virus (MDV), infectious bursal disease virus, reticuloendotheliosis virus, adenovirus, or reovirus. It has been reported that pathogenesis of MDV is enhanced by CIAV (DeBoer et al., 1989, p. 28 In Proceedings of the 38th Western Poultry Diseases Conference, Tempe, Ariz.). Further, it has been reported that CIAV aggravates the signs of infectious bursal disease (Rosenberger et al., 1989, *Avian Dis.* 33: 707–713). Additionally, subclinical CIAV infection in older chickens is correlated with decreased performance in broiler flocks (McNulty et al., 1991, *Avian Dis.* 35: 26314 268). CIAV is highly resistant to environmental inactivation and some common disinfectants, characteristics that may potentiate disease transmission. The economic impact of CIAV infection on the poultry industry is reflected by mortality of 10% to 30% in disease outbreaks, a possible role in vaccine failures, and lower performance of infected flocks due to subclinical infection.

CIAV typically can be propagated in embryonated eggs and lymphoblastoid cell lines, such as the Marek's disease virus-transformed chicken lymphoblastoid cell line MDCC-MSB-1 (MSB-1; Akiyama et al., 1974, *Biken J.* 17: 105–116), but not in chicken embryo fibroblasts, chicken kidney cells, or other primary chicken cells. However, not all strains can be adapted to cell culture as evidenced by the CIA-1 strain (Lucio et al., 1990, *Avian Dis.* 34: 14614 153). Thus, biological differences may exist between strains.

CIAV is a small, non-enveloped icosahedral virus of 25 nm diameter, and contains a genome consisting of 2.3 kb circular, single-stranded DNA. Two polypeptides have been detected in purified virus preparations; a major polypeptide of about 50 kilodaltons (kDa) termed VP1, and a 24 kDa polypeptide termed VP2. These two polypeptides together form a major epitope for the production of virus-neutralizing antibodies. Genomic DNA sequences of several different isolates of CIAV have been reported. Isolate Cux-1 was sequenced by Noteborn et al. (1991, *J. Virol.* 65: 3131–3139; herein incorporated by reference) revealing 3 open reading frames (ORFS) that potentially encode polypeptides of 51.6 kDa, 24.0 kDa, and 13.6 kDa. There was only one promoter-enhancer region upstream of the ORFs, and a single polyadenylation signal downstream of the ORFs. A single unspliced mRNA of 2100 bases is transcribed from the Cux-1 genome (Noteborn et al., 1992, *Gene* 118: 267–271; herein incorporated by reference). Another group also sequenced the Cux-1 strain; however, differences were noted between their sequence data and those from Noteborn et al. (Meehan et al., 1992, *Arch. Virol.* 124: 301–319; herein incorporated by reference). The nucleotide sequence of strain 26P4, isolated in the U.S.A., also showed a number of nucleotide differences when compared with sequences of Cux-1 (Claessens et al., 1991, *J. Gen. Virol.* 72: 2003–2006; herein incorporated by reference). Despite the differences in nucleotide sequences found in various isolates from around the world, only minor differences in amino acid sequences have been noted. For these reasons, it has been assumed that CIAV is a highly conserved virus.

Exposing hens to CIAV may induce maternal antibody in chickens which may help protect against CIAV infections in their progeny. However, such vaccination with any of the CIAV strains has inherent problems including the potential of vertical (through the egg) transmission, and contamination of the environment. It is therefore desirable to develop a vaccine having as the immunogen a purified polypeptide(s) associated with CIAV.

2. SUMMARY OF THE INVENTION

According to the present invention, three open reading frames (ORF-1, ORF-2, ORF-3) , have been identified in the genome of CIAV strain CIA-1 , a non-cell culture-adapted strain. Comparing the 3 ORFs from CIA-1 with other CIAV isolates, particularly the prototypic cell culture-adapted strain Cux-1 (C), reveals that the polypeptide (VP1) encoded by ORF-1 contains at least 4 unique amino acid changes that could potentially affect conformational changes in VP1. Because CIA-1 fails to replicate in the Cornell subline of MSB-1 cells in culture, it is likely that one or more unique amino acid changes in VP1 is responsible for the differences in viral biology affecting cell pathology ("pathogenicity"). Additionally, the inability of CIA-1 to infect certain cultured cell lines ("cell tropism") indicates that one or more unique amino acid changes in VP1 is responsible for such tropism. Accordingly, one object of the present invention is to identify the polypeptide(s) involved in the observed differences in phenotype of this novel isolate.

Another object of the present invention is to provide an approach to control CIAV infection by interfering with the establishment of infection, or disease progression, in poultry susceptible to CIAV.

Another object of the present invention is to prevent the development of disease caused by CIAV by inducing protective antibody and/or a cell-mediated immune response to one or more polypeptides which are associated with the virus.

Another object of the present invention is to induce protective antibody and/or a cell-mediated immune response to a viral polypeptide wherein the polypeptide reflects wild type strains of CIAV more so than that in cell culture-adapted strains.

Another object of the present invention is to provide one or more nucleic acid sequences, encoding respective CIAV polypeptide(s), which can be inserted for expression into a recombinant viral vector, or introduced directly into susceptible chickens.

Other objects and advantages of the invention will become readily apparent from the ensuing description.

3. BRIEF DESCRIPTION OF THE FIGURES

FIG. 1 is a schematic representation of the organization of ORF-1, ORF-2, ORF-3, the promoter-enhancer region (P-E) and the polyadenylation signal (PAS) in the CIA-1 genome.

FIG. 2 is a hydrophilicity plot for the polypeptide encoded by CIA-1 ORF-1. Note three changes: At position A, there are 2 turns in the secondary structure versus 3 for Cux-1. At position B, a hydrophilicity shift in the CIA-1 polypeptide is indicated. At position C, Cux-1 has an additional turn compared to the CIA-1 polypeptide.

FIG. 5 is a schematic representation showing construction of various chimeric viral clones using CIA-1 DNA and Cux-1; and an adjoining table showing the percentage of MSB-1 (S) cells versus MSB-1 (L) cells infected with the viral clones which were positive for VP3 by immunofluorescence assay. Dashes indicate a negative result in immunofluorescence; n.d. indicates that immunofluorescence assays were not performed.

4. DETAILED DESCRIPTION OF THE INVENTION

Figure 1:
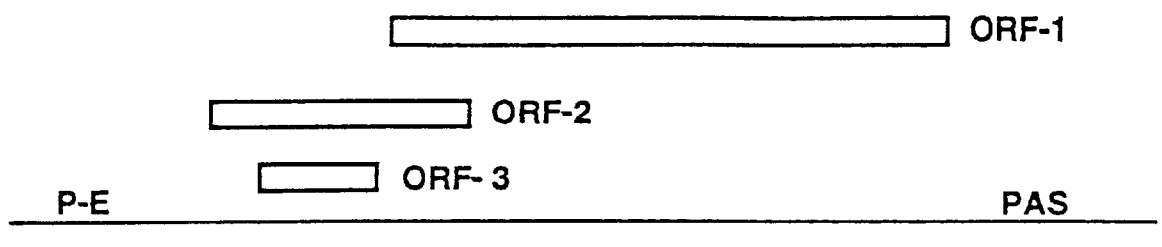

The CIAV genome is a circular single stranded molecule of about 2,300 nucleotides in length. It consists of three overlapping reading frames (ORFs) which are identified herein as ORF-1, ORF-2, and ORF-3, and potentially encode polypeptides of 51.6 kDa (VP1), 24.0 kDa (VP1), and 13.6 kDa (VP3), respectively. As positioned in the genome, the three ORFs either partially or completely overlap one another and appear to use the same upstream region as a promoter and enhancer, and the same polyadenylation signal located downstream of the ORFs (FIG. 1).

Presently, the process by which CIAV causes chicken infectious anemia is poorly understood. When CIA-1 is introduced into susceptible 1-day-old chicks, CIA-1 produced signs and lesions characteristic of chicken infectious anemia including low hematocrit values, depletion of erythrocytes and lymphoid cells in the bone marrow, depletion of lymphoid cells of the medulla and the cortex of the thymus (herein referred as T-cells), and inflammatory changes in the liver, heart and kidney (Lucio et al., 1990, *Avian Dis.* 34: 146–153). One or more of the polypeptides encoded by the CIAV ORFs may play a role in the pathogenesis of chicken infectious anemia by facilitating invasion into susceptible cells, and/or initiating T-cell apoptosis.

The term "unique amino acid change", for purposes of the specification and claims, refers to one or more changes or amino acid substitutions present in the CIA-1 VP1 amino acid sequence, as compared to the amino acid sequence of the prototypic cell culture-adapted strain Cux-1 (C) as well as that of some other cell culture-adapted strains.

The term "polypeptide" is used herein, for purposes of the specification and claims, to refer to a chain of amino acids, having a biological function, and does not refer to a specific length of the chain. Thus, polypeptide may be used to refer to peptides, oligopeptides, and proteins containing the amino acid changes unique to CIA-1 as compared to Cux-1, Conn and GA strains of CIAV. Further, if required, the polypeptide can be modified in vivo or in vitro by, for example, glycosylation, amidation, phosphorylation, carboxylation, or substitution without changing the primary biological function.

Amino acid substitutions in a polypeptide, particularly resulting in a change in side group polarity and/or charge, can be reflected in the secondary structure of the polypeptide, and thus can alter biological activity of that polypeptide or the virion bearing the polypeptide. This is important, as the deduced amino acid sequence of the CIA-1 polypeptide VP1 of the present invention shows such amino acid substitutions when compared to the VP1 polypeptide of some cell culture-adapted CIAV strains. Also, amino acid substitutions are present in the CIA-1 VP2 and VP3 polypeptides. Functional equivalents of the polypeptides disclosed herein, i.e. polypeptides with the same amino acid sequence, or amino acid replacements between related amino acids (i.e. having similar polarity and/or charge), are within the scope of this invention.

Nucleic acid sequences encoding such functional equivalents are included within the scope of this invention: As well known in the art of recombinant DNA technology for the preparation and modification of nucleic acid sequences, degeneracy of the genetic code permits substitution of bases in a codon resulting in another codon which still encodes for the same amino acid. Mutagenesis, insertion, and or synthesis can be used to generate a nucleic acid sequence derivative (functional equivalent) of ORF-1, ORF-2 or ORF-3 which would encode the respective functional equivalent polypeptide.

Thus, the information provided in SEQ ID NOs:1–3 allows a person skilled in the art to isolate and identify nucleic acid sequences encoding functional equivalent polypeptides having the biological function and immunologic activity of the polypeptides disclosed in SEQ ID NOs:1–3. Using methods and procedures in accordance with the present invention, and known to those skilled in the art, including virus propagation, nucleic acid sequence amplification, cloning, sequencing, restriction enzyme analysis, and transfection, DNA may be obtained from other CIAV strains to identify ORFs which can encode a polypeptide functionally equivalent to the polypeptides of the present invention disclosed in SEQ ID NOs:1–3.

Additionally, fragments of the nucleic acid sequences disclosed in SEQ ID NOs:1–3 (i.e., DNA subsequences) can be used to encode peptides (a subsequence of the disclosed polypeptides and containing one or more of the amino acid changes of CIA-1 ) having one or more immunoreactive/antigenic determinants and/or determinant associated with equivalent biological function of the polypeptides disclosed in SEQ ID NOs:1–3. Thus, peptides that are included within this scope of this invention include those having one or more determinants characteristic of the polypeptides that specifically include one or more of the amino acid changes in the respective polypeptide of CIA-1 as disclosed in the invention (amino acid residue 22, 75, 139, and/or 144 of the polypeptide VP1; hereinafter referred to as "the amino acid changes in CIA-1"), and include the capability of eliciting an immune response in chickens. Any such modifications of the nucleic acid sequences of the present invention, and the polypeptides they encode, will be described in more detail in the embodiments to follow.

The present invention particularly relates to the identification and characterization of ORF-1, and its gene product VP1, from CIAV isolate CIA-1. It is noted that CIA-1 is propagated in chicks, and the cells of infected chicks are used to isolate the virus; whereas other CIAV strains, such as Cux-1, GA, and Conn, are able to, and were propagated in cell culture in vitro. The relative positioning of the ORFs is represented in FIG. 1. DNA was isolated and then amplified by polymerase chain reaction to facilitate cloning, sequencing, and expression. From the DNA sequence of CIA-1, three open reading frames (ORF-1, SEQ ID NO:1; ORF-2, SEQ ID NO:2; and ORF-3, SEQ ID NO:3) were identified which can encode polypeptides of about 51 kDa (VP1), 24 kDa (VP2) and 13 kDa (VP3) in molecular size, respectively.

Because of the lack of effective drugs to therapeutically treat chickens with chicken infectious anemia, and with problems such as vertical transmission if the virus itself is used as a vaccine, alternative approaches to controlling chicken infectious anemia should be considered. One embodiment of the present invention is to control the development of chicken infectious anemia by inhibiting the development of sequelae in CIAV-infected cells. Therefore, in one variation of this embodiment, one or more of the novel polypeptides of the present invention are used to immunize chickens to induce an immune response which may block infection, and/or initiation of T-cell apoptosis upon infection, by CIAV. In another variation of this embodiment, the DNA encoding one or more of VP1, VP2, or VP3 can be injected directly into the tissue of chicks, or embryos between 17 and 21 days of incubation. In another variation of the embodiment, one or more of the three ORFs can be inserted in a direction, and operatively linked to one or more control elements, in any vector useful as a vaccine by itself or as introduced in a live or attenuated microorganism, wherein the respective ORF is expressed to produce its respective polypeptide. Thus, for example, a recombinant viral vaccine vector can be constructed which may either be inoculated into embryos in ovo or into chicks directly after hatching. In yet another variation of this embodiment, one or more of the three ORFs can be inserted in a plasmid vector. The recombinant plasmid is constructed such that in vivo transcription is regulated by either an inducible promoter or a constitutive promoter. The recombinant plasmid is then injected into embryos in ovo or into chicks directly after hatching. Another variation of this embodiment involves the development of transgenic chickens which express one or more of the three ORFs, wherein the transcription is under the control of an inducible promoter or a constitutive promoter.

A second embodiment of the present invention relates to vaccination with one or more of the polypeptides disclosed in SEQ ID NOs:1–3. In one variation of this embodiment, chicks or chickens are immunized with a vaccine comprising one or more of the polypeptides which may elicit protection by inducing an immune response that would recognize either CIAV challenge or cells infected with CIAV. In another variation of this embodiment, one or more peptides derived from the polypeptides disclosed herein (and containing one or more of the amino acid changes as found in CIA-1) are used as the immunogen in a vaccine composition. Alternatively, the vaccine may comprise a vector, such as a recombinant viral vector, containing one or more ORFs under the control of a strong promoter so that the respective polypeptide is expressed. In another variation of this embodiment, the vaccine comprises a vector such as a recombinant viral vector, containing those nucleotide sequence fragments of one or more of the ORFs, wherein the nucleotide sequence fragment codes for epitopes inducing humoral (approximately 15 amino acids) or cell-mediated (approximately 9 amino acids) immune responses which contain one or more amino acid changes in CIA-1. The determination of regions containing epitopes inducing humoral immunity can be based on hydrophilicity and secondary structure analyses (See for example, Hopp et al., 1981, Proc. Natl. Acad. Sci. USA 78: 3824–3828; Chou et al., 1978, Adv. Enzymol. Relat. Areas Mol. Biol. 47: 45–148). Likewise, determination of epitopes important in cell-mediated immunity can be derived on the basis of analyses of the amino acid structure including amphilicity (See for example, Berzofsky, 1987, Science 235: 1059–1062). Cleavage of the polypeptides with certain enzymes, such as Cathepsin D, is known to generate $NH_2$-terminal fragments/peptides having amino acid residues recognized by the major histo-compatibility complex on the surface of antigen-presenting cells (van Noort et al., 1989, J. Biol. Chem. 264: 14159, 1989).

EXAMPLE 1

Isolation and Characterization of ORFs 1–3

Cell-culture-adapted strains Cux-1(C) (Chandratilleke et al., 1991, Avian Dis. 35: 854–862), GA (Goodwin et al., 1989, pp.21–23 in Proc. 38th Western Poultry Disease Conference, Temple, Ariz.), and Conn served as the source for isolation of viral genomic DNA. These strains were cultivated in the Marek's disease virus-transformed T cell line MDCC-MSB-1 ("MSB-1"; Yuasa, 1983, Natl. Inst. Anim. Health Q. 23: 13–20). CIA-1, an isolate that does not replicate in the Cornell subline of MSB-1 cells (in contrast with the Cux-1, Conn, and GA strains of CIAV; Lucio et al., 1990, supra) and propagated in one-day-old chicks, served as a source of viral genomic DNA. The one day old chickens, shown experimentally to be free of antibodies against CIAV, were inoculated intramuscularly (Lucio et al., 1990, supra). Liver cells, thymocytes, and bone marrow were obtained from these infected chicks from which CIA-1 was isolated.

Virus was isolated from infected MSB-1 cells according to the method of Hirt (1967, J. Mol. Biol. 26: 365–369). The method involves lysing the infected cells by treatment with sodium dodecyl sulfate, followed by precipitation of high molecular weight cellular DNA at high salt concentration (1M NaCl). Low molecular weight viral RF (replicative form; double stranded) DNA was then purified from the lysis buffer by phenol-chloroform extraction and ethanol precipitation. Virus was isolated from CIA-1 infected chick cells by isolating infected tissue, preparing the cells as a 10% suspension, boiling the cell suspensions for 10 minutes, incubating the boiled suspension for 1 hour with 100 μg proteinase K/ml at 50° C., inactivating the enzyme at 95° C. for 10 minutes, and then purifying the low molecular weight RF DNA by phenol-chloroform extraction and ethanol precipitation.

Amplification of DNA may be accomplished by any one of the methods commercially available. For example, the polymerase chain reaction may be used to amplify the DNA.

Once the primers have hybridized to opposite strands of the target DNA, the temperature is raised to permit replication of the specific segment of DNA across the region between the two primers by a thermostable DNA polymerase. Then the reaction is thermocycled so that at each cycle the amount of DNA representing they sequences between the two primers is doubled, and specific amplification of the CIAV DNA sequences results.

The genomes of all strains of CIAV can be amplified from RF DNA using the polymerase chain reaction according to the methods of Soiné et al. (1993, *Avian Dis.* 37: 467–476; the disclosure of which is herein incorporated by reference). A pair of primers (SEQ ID NO:4 and SEQ ID NO:5) was used to amplify a 1500 base pair (bp) stretch of RF DNA. A second pair of primers (SEQ ID NO:6 and SEQ ID NO:7) was used to amplify the remaining 800 bp of the RF DNA. The reactions were carried out as follows. DNA to be amplified (≈1 μg of genomic DNA) was distributed in 0.5 ml microfuge tubes and the volume was adjusted to 100 μl by adding a reaction mixture comprising 0.2 mM dNTPs (DATP, dCTP, dGTP, dTTP), 1 μM of each positive and negative oligonucleotide primer, 2 units of thermostable DNA polymerase, and buffer containing 50 mM KCl, 10 mM Tris-HCl pH 8.3, 0.15 mM $MgCl_2$, 0.001% (wt:vol) gelatin. A layer of mineral oil, approximately 70 μl, is added to overlay the mixture in each tube and then the tubes are placed in the thermal cycler. Thirty to thirty-five cycles are generally sufficient for viral DNA amplification. The thermal cycles were started with a long denaturation step of 5 minutes at 94° C. Amplification of DNA was achieved in a 30 cycle run, the first five cycles with 1 minute denaturation at 94° C., 2 minutes annealing at 65° C., and 2 minutes extension at 72° C. The next five cycles were performed with 1 minute at 94° C., 1 minute at 60° C., and 2 minutes at 72° C. This was followed by a final extension step of 5 minutes at 72° C. After chloroform extraction of the amplified products, the size of the resultant products may be confirmed by agarose gel electrophoresis.

The amplified, purified 1500 bp and 800 bp fragments were then digested with both EcoRI and BamHI and ligated together. The preparation was then again digested with EcoRI and subsequently cloned into EcoRI-digested pBluescript KSII™ (Soiné et al., 1993, supra). The plasmids were used to transform *Escherichia coli* strain DH5α. The respective clones of Cux-1, GA, Conn, and CIA-1 were sequenced by the chain termination method (Sanger et al., 1977, *Proc. Natl. Acad. Sci. USA* 74: 5463–5467). Subclones providing overlapping sequence stretches on either the plus or minus strand were constructed and sequenced using the T3 and T7 promoter primer sites. Initially, different colonies were sequenced for the subclones to determine if the cloning by polymerase chain amplification had caused variation. However, no differences were encountered.

In analyzing the nucleotide sequences, the respective sequences of the CIA-1, GA, Conn, and Cux-1 (C) clones were compared to the sequence determined by Noteborn et al. (Cux-1 (N); 1991, supra). The CIA-1 genomic clone, as compared to Cux-1 (C) had 42 nucleotide changes, with 36 of them in the coding regions of the three ORFs. A major change was observed in the promoterenhancer region of CIA-1, as there were only 4 repeat units (a repeat unit having the sequence CGTACAGGGGGGTACGTCATC), instead of 5, resulting in a length of 2298 bases for CIA-1 compared to 2319 bases for Cux-1 (C). The first repeat starts at nucleotide 144 in both strains. By analyzing the sequences of CIA-1 and Cux-1 (N) for FokI restriction enzyme sites, it was determined that the third repeat is missing. Cell culture-adapted GA strain, Conn strain, and Cux-1 (C) strain had 3, 5, and 1 nucleotide changes in the coding region, respectively. These three strains all showed 5 repeat units in the promoter-enhancer region, suggesting that a fifth repeat is selected for by repeated culture.

The promoter-enhancer region of CIA-1 was searched for binding sites of known transcription factors. The transcription factor binding sites found correlate with those described previously (Noteborn et al., supra; Meehan et al., 1992, supra) and include sites for TFIID (location: nucleotides 301–308), CCAAT-TF (nucleotides 239–245), SP1 (nucleotides 284–289), ATF (nucleotides 157–162, 178–183, 211–216, 232–237), CREB (nucleotides 270–276). A poly(A) signal was located downstream of the ORFs (nucleotides 2266–2271).

The complete amino acid sequence of polypeptides VP1, VP1, and VP3 are shown in SEQ ID NO:1–3, respectively. In comparing the deduced amino acid sequences of the CIA-1 vs. Cux-1 (C) ORFs and other known sequences for cell culture-adapted CIAV strains (Table 1), revealed 4 unique amino acid changes in VP1 encoded by CIA-1 ORF-1; 2 amino acid changes in VP2 not present in most cell culture-adapted CIAV strains; and 1 amino acid change in VP3 not present in most cell culture-adapted CIAV strains (underlined).

TABLE 1

| | Position | CIA-1 | GA | Conn | Cux-1 (C) | Cux-1 (N) | Cux-1 (M) | 26P4 |
|---|---|---|---|---|---|---|---|---|
| VP1 | 22 | <u>Asn</u> | His | His | His | His | His | His |
| | 75 | <u>Ile</u> | Val | Val | Val | Val | Val | Val |
| | 139 | <u>Gln</u> | Lys | Lys | Lys | Lys | Lys | Lys |
| | 144 | <u>Gln</u> | Asp | Asn | Asp | Asp | Asp | Glu |
| VP2 | 153 | <u>Val</u> | Ala | Ala | Ala | Ala | Val | Val |
| VP3 | 118 | <u>Cys</u> | Arg | Arg | Arg | Arg | Cys | Cys |

EXAMPLE 2

Biological properties of CIA-1

CIA-1 has failed to replicate in both the Cornell subline of MSB-1 (L) cells (Lucio et al., 1990, supra) and in CU147 cells (Lucio, unpublished). The latter cell line is more susceptible to replication than MSB-1 (L) cells. One or more of the amino acid sequence differences observed in the CIA-1 VP1 polypeptide is suspected to play a role in the lack of CIA-1 to replicate in cell culture. For example, 4 amino acid changes were noted in the 50 kDa polypeptide, VP1, encoded by CIA-1 ORF-1. The 50 kDa polypeptide is thought to be the viral capsid protein (Todd et al., 1990, *J. Gen. Virol.* 71: 819–823). Thus, for example, conformational changes in the capsid protein may affect such processes of infection including the adsorption and penetration of the virus into susceptible cells, and subsequent uncoating of the viral genome. To implicate the amino acid changes in VP1 with lack of replication in cell culture, transfection experiments were performed with the CIA-1 RF (double-stranded circularized) DNA. As a control, parallel transfections were done using Cux-1 RF DNA. The viral RF DNA from an infectious clone, when transfected into susceptible cells, should start replication and transcription. Virus replication can thus be evidenced by the detection of viral protein production in infected cells, such as by immunofluorescence. The presence of viral DNA in the infected cells combined with the absence of viral protein production is evidence that the inability of CIA-1 to replicate in cultured cells may be due to one or more of the unique amino acids found in the amino acid sequence of CIA-1 VP1.

Transfections were done by electroporation using an electroporator at 300 V and a capacitance of 960 µF (Schat et al., 1992, Avian Dis. 36: 432–439, the disclosure of which is herein incorporated by reference). MSB-1 cells were centrifuged through a cell separation gradient 24 hours prior to transfection. Prior to electroporation, the cells were washed once in PBS and resuspended in LM-base medium without serum and adjusted to a concentration of $1\times10^6$/ml. For electroporation, 10 µl of CIAV (either CIA-1 or Cux-1) RF DNA in water was added to 400 µl of cell suspensions. Directly before and after the electroporation, the cells were held on ice for 10 minutes. The cells were diluted into 4 ml of LM-base medium supplemented with 10% serum, and then transferred to 24-well plates. At 14 days post transfection, the cells were centrifuged at 3000 rpm for 30 minutes to pellet the cells and other particles. A portion of the supernatant fluid was ultracentrifuged for 5 hours at 90,000×g and the pellet was saved. The pellet and the original cell culture supernatant fluid was used to infect MSB-1 cells in 24-well plates.

Five µg of plasmid pNL1 (or pRC/LTRLacZ), which contains the lacZ gene (Schat et al., 1992, Avian Dis. 36: 432–439), was co-transfected with the CIAV RF DNA to determine the efficiency of electroporation. LacZ expression was determined by measuring beta-galactosidase activity using the substrate 5-bromo-4-chloro-3-indolyl-beta-D-galactopyranoside (X-gal) at 2 days post transfection. Cells were washed and resuspended in PBS at a concentration of $1\times10^7$ cells/ml. The cells, at $5\times10^4$, were air-dried onto slides and fixed for 5 minutes in 0.05M phosphate buffer, pH 7.4, containing 0.2% (v/v) glutaraldehyde, 2% (v/v) formaldehyde, and 2 mM $MgCl_2$. The cells were then incubated at 37° C. for up to 16 hours in a solution containing 0.5 mg X-gal/ml, 5 mM potassium ferricyanide, 5 mM potassium ferrocyanide, and 2 mM $MgCl_2$ in a 0.05M phosphate buffer, pH 7.4.

The Cornell subline of MSB-1 (L) cells transfected with CIAV RF DNA were examined every 3 days post transfection for viral protein production using immunofluorescence. The Cornell subline of MSB-1 (L) cells, electroporated with DNA other than CIAV DNA, were used as a negative control. Transfected cells were washed once in PBS, then $5\times10^4$ cells per well were dropped on a 12-well slide and air-dried. After 10 minutes fixation in acetone at room temperature, the cells were incubated at room temperature for 30 minutes with monoclonal antibody 51.3, an antibody specific for CIAV protein VP3 (Chandratilleke et al., 1991, supra). This antibody has been used to demonstrate the presence of virus antigens in thymus tissues obtained from chickens infected with CIA-1 (Hu et al., 1993, Avian Dis. 37: 157–169, and 37: 492–500). Slides were washed with PPS and then incubated for incubated for 30 minutes with FITC-conjugated rabbit-anti-mouse antibody. After the second washing step, the slides were mounted with glycerin-buffer (90% glycerin, 10% Tris-HCl buffer, pH 8.7) and inspected under a microscope for fluorescence.

Transfection of the Cornell subline of MSB-1 cells with circularized Cux-1 RF DNA resulted in specific fluorescence at 5 days post transfection. Positive cells became more numerous until 15 days post transfection. To determine if infectious virus could be recovered after transfection, supernatant fluid obtained at 15 days post transfection was used as a source of inoculum to infect the MSB-1 cells. In addition, the MSB-1 cells were infected with material pelleted by ultracentrifugation. In each instance, virus-positive cells could be detected by immunofluorescence. Cells infected with the pelleted material were positive for immunofluorescence 5 days earlier, post transfection, than cells in which the supernatant fluid was used as the inoculum.

In contrast, transfection of the Cornell subline of MSB-1 cells with CIA-1 RF DNA repeatedly did not result in the establishment of virus replication as evidenced by the absence of immunofluorescence. However, 0.01 to 0.03% of the MSB-1 cells were positive for beta-galactosidase, indicating that pNL1 was present and thus transfections were adequate.

Polymerase chain reaction was used to confirm that by electroporation CIA-1 DNA was successfully transfected into the MSB-1 (L) cells. At 6 days post transfection, the transfected cells were washed 3× in PBS, and DNA was extracted. As a template for DNA amplification, 100 ng of DNA was used. The primers shown in SEQ ID NO:4 and SEQ ID NO:5 were used to amplify the 1.5 kb fragment of the genome. DNA extracted from non-transformed MSB-1 cells served as a negative control. Conditions for amplification, along with agarose gel electrophoresis methods for confirming the size of the amplified fragment, have been described previously (See for example, Soiné et al., 1993, supra; and Example 1). At 6 days post transfection, Cux-1 RF DNA transfected cells, but not mock-transfected MSB-1 cells, were strongly positive for the presence of CIAV DNA as indicated by the amount of amplified 1,500 bp fragment DNA visualized by agarose gel electrophoresis with ethidium bromide staining. CIA-1 RF DNA transfected cells also were positive for the presence of CIAV DNA, but the amount of amplified 1,500 bp fragment was less than that visualized for Cux-1 infected cells. However, the presence of the amplified 1,500 bp fragment from CIA-1 RF DNA transfected cells indicates that the viral DNA was present in at least some of the transfected cells.

EXAMPLE 3

Figure 3:
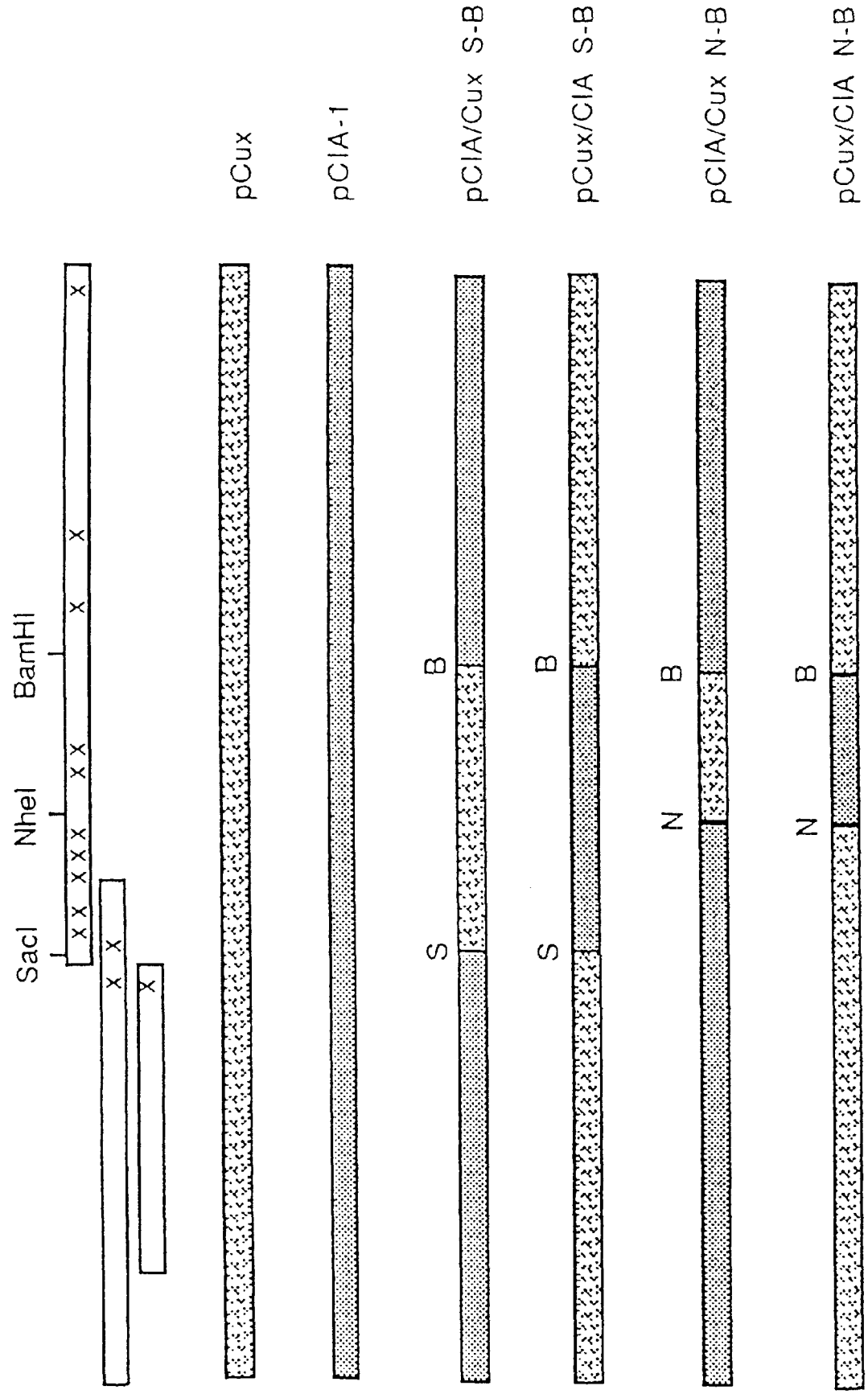
FIG. 3 is a schematic representation showing construction of various chimeric viral clones using CIA-1 DNA and Cux-1 DNA.
Figure 4:
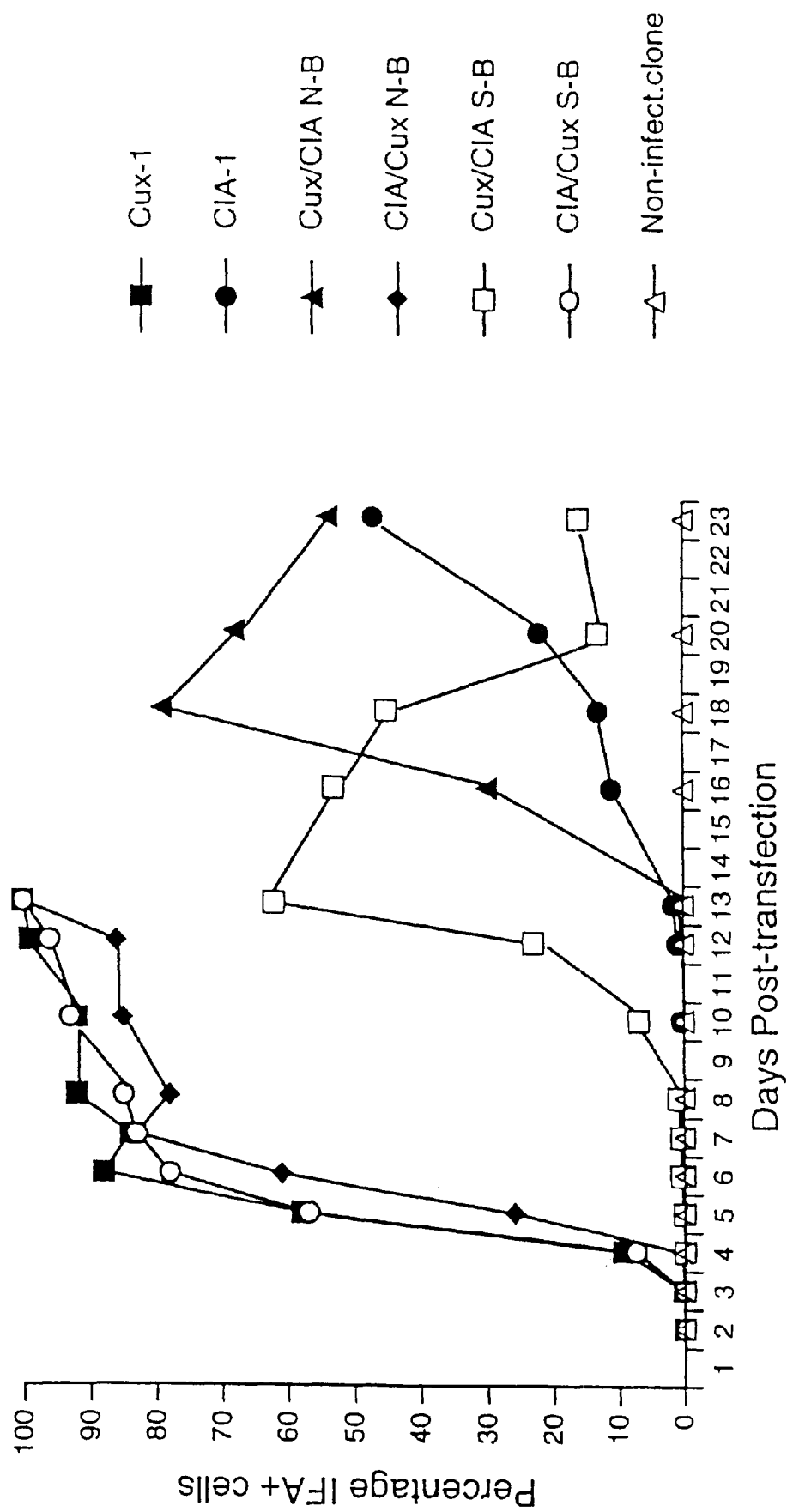
FIG. 4 is a graph indicating the percentage of cells, transfected with the respective chimeric viral clone, which are positive for CIAV protein production by immunofluorescence as plotted against the number of days post-transfection.

Identification of the polypeptide which affects CIA-1 biology-virus replication and cell pathology This embodiment is directed to the construction of chimeric CIAV viruses to determine if the unique amino acids in the sequence of CIA-1 VP1 are the primary mediators of differences of virus replication in, and pathology of, CIA-1-infected cells; as compared to Cux-1, a prototypic cell culture-adapted strain. In the MSB-1 (S) cells, CIA-1 was found to be significantly less cytopathic than the Cux-1 (C) isolate. As illustrated in FIG. 4, infections at equal MOIs (multiplicity of infection) showed that Cux-1 infections resulted in high levels (60–90%) of infected cells at 4 to 6 days post infection. In contrast, CIA-1 infections normally require 10–14 days to attain comparable levels (60–90%). DNA isolated from CIAV strain Cux-1 (Noteborn et al., 1991, supra) and DNA from CIA-1 were digested with various restriction enzyme combinations, and specific portions of Cux-1 DNA and CIA-1 DNA were ligated together in constructing four chimeric CIAV viral clones (FIG. 3). Nucleotide numbering for Cux-1 sequence refers to the numbering and published sequence of Cux-i (Noteborn et al., 1991, supra). Nucleotide numbering for CIA-1 sequence refers to the numbering and sequence of CIA-1 as shown in SEQ ID NO:1.

As illustrated in FIG. 3, chimeric viral clones pCIA/Cux S-B and pCux/CIA S-B were formed by digesting Cux-1 DNA and CIA-1 DNA with SacI and BamHI. Thus, the Cux-1 nucleotide sequence beginning from the SacI site (5' end is nucleotide 868) to the BamHI site (3' end is nucleotide 1507) was removed from Cux-1 sequence and then ligated into CIA-1 sequence at the CIA-1 SacI site (3' end is nucleotide 846) and CIA-1 BamHI site (5' end is nucleotide 1487) in forming pCIA/Cux S-B. Similarly, the CIA-1 nucleotide sequence beginning from the SacI site (5' end is nucleotide 847) to the BamHI site (3' end is nucleotide 1486) was removed from CIA-1 sequence and then ligated into Cux-1 sequence at the Cux-1 SacI site (3' end is nucleotide 867) and Cux-1 BamHI site (5' end is nucleotide 1508) in forming pCux/CIA S-B.

As illustrated in FIG. 3, chimeric viral clones pCIA/Cux N-B and pCux/CIA N-B were formed by digesting Cux-1 DNA and CIA-1 DNA with NheI and BamHI. Thus, the Cux-1 nucleotide sequence beginning from the NheI site (5' end is nucleotide 1192) to the BamHI site (3' end is nucleotide 1507) was removed from Cux-1 sequence and then ligated into CIA-1 sequence at the CIA-1 NheI site (3' end is nucleotide 1171) and CIA-1 BamHI site (5' end is nucleotide 1487) in forming pCIA/Cux N-B. Similarly, the CIA-1 nucleotide sequence beginning from the NheI site (5' end is nucleotide 1172) to the BamHI site (3' end is nucleotide 1486) was removed from CIA-1 sequence and then ligated into Cux-1 sequence at the Cux-1 NheI site (3' end is nucleotide 1191) and Cux-1 BamHI site (5' end is nucleotide 1508) in forming pCux/CIA N-B. The construction of all chimeric clones was verified by nucleotide sequencing.

In accordance with the methods described in Example 2, the chimeric viral clones were separately introduced into MSB-1 (S) cells. The respective infected MSB-1 (S) cells were then analyzed for virus replication, as detected by viral protein production using immunofluorescence (See Example 2). The absence of viral protein production is evidence of the inability of the particular chimeric clone to replicate in cultured cells. FIG. 4 is a graph indicating the percentage of cells, transfected with the respective chimeric viral clones, which are positive for CIAV protein production by immunofluorescence as plotted against the number of days post-transfection. As indicated in FIG. 4, Cux-1, chimeric clone CIA/Cux S-B, and chimeric clone CIA/Cux N-B demonstrated a higher percentage of cells positive for CIAV protein production/viral replication, and several days earlier post-transfection, than cells containing CIA-1, chimeric clone Cux/CIA S-B, and chimeric clone Cux/CIA N-B. From these observations, it can be concluded that a) differences in the amino acid sequence of CIA-1 VP1, as compared to that of Cux-1 VP1, are responsible for the observed phenotypic differences of CIA-1 infection; and b) such amino acid sequence differences can be localized to the unique amino acids at positions 139 and/or 144 of CIA-1 VP1 (what appears to be a hypervariable region), and is the primary mediator of the phenotypic differences of CIA-1 (differences of virus replication in, and pathology of, CIA-1-infected cells, as compared to Cux-1).

EXAMPLE 4

Identification of the polypeptide which affects CIA-1 biology-cell tropism

It has been observed that some non-cell culture adapted ("wild type") isolates do not replicate in certain cell lines used for passaging cell culture-adapted strains of CIAV. The basis for such cell tropisms is unclear. This embodiment is directed to the construction of chimeric CIAV viruses to determine if the unique amino acids in the sequence of CIA-1 VP1 are the primary mediators of differences of in cell tropism of CIA-1; as compared to Cux-1, a prototypic cell culture-adapted strain.

In accordance with the methods described in Examples 2 and 3, chimeric viral clones (chimeras of CIA-1 and Cux-1) were constructed and thesubeparately introduced into two different sublines of MSB-1 cells (FIG. 5). The left side of FIG. 5 shows the restriction sites used, and the restriction fragments transferred between CIA-1 and Cux-1 (C), for the construction of the chimeric viral clones. The adjoining table in FIG. 5 shows the percentage of cells positive for VP3 by immunofluorescence assay, at selected time points. Transfected cells were split every two days and carried for nine to ten passages, and examined by immunofluorescence every one to three days.

Successful transfection of MSB-1 (L) cells with viral clones was verified by the observance of cells positive by immunofluorescence at 60 hours post-transfection. However, in many cases, detectable expression of VP3 was only transient and productive infections did not develop. As shown in FIG. 5, neither CIA-1, nor any of the CIA-1 chimeric viral clones were able to initiate infections in MSB-1 (L) cells. Thus, CIA-1 VP1 regions are sufficient to block viral replication in/re-infection of MSB-1 (L) cells. Also shown in FIG. 5, the Cux-1 based-chimeras containing portions of the CIA-1 genome were able to initiate infections in MSB-1 (L) cells, with the notable exception of the chimeric viral clone which contained CIA-1 sequences comprising the first one third of the VP1 coding region. From these observations, it can be concluded that a) replacement of this region of VP1 of Cux-1 with CIA-1 sequences results in a non-infectious clone (in MSB-1 (L) cells); b) differences in the amino acid sequence of CIA-1 VP1, as compared to that of Cux-1 VP1, are responsible for the observed phenotypic differences of CIA-1 infection (or lack of); and c) that unlike the finding that the VP1 polypeptide portion encoded by the NheI to BamHI region is the primary mediator related to pathogenic potential, the VP1 polypeptide portion (amino acid sequence differences) encoded by the SacI to BamHI region is the primary mediator in determining the inability of CIA-1 to infect MSB-1 (L) cells.

Another subline of MSB-1 cells, MSB-1 (S) was used to determine if the inability of CIA-1, or chimeric clones containing a restriction fragment comprising at least the first one third of the encoding region for CIA-1 VP1, to infect MSB-1 (L) cells is a block of viral replication, or the inability of virions formed post-transfection to infect MSB-1 (L) cells. All chimeric clones, as shown in FIG. 5, are capable of infecting MSB-1 (S) cells if transfected directly into cells of that subline. In this experiment, supernatants from infected MSB-1 (L) cell cultures were taken at 60 hours post-transfection, filtered (0.2 μm) and added to individual cultures of MSB-1 (S) cells. As shown by the corresponding table in FIG. 5, CIA-1 and the chimeric viral clone containing all of the CIA-1 sequence encoding a full length VP1, each failed to produce an infection in MSB-1 (S) cells. This suggests that there is a block in viral replication in infected MSB-1 (L) cells. However, in certain instances, infections were detected in MSB-1 (S) cells. This is evidence that the supernatant from some of the MSB-1 (L) cell infections (i.e., those that were transfected with some of the chimeric viral clones containing partial CIA-1 VP1 encoding sequences) contained infectious, extracellular virus, and thus replication in MSB-1 (L) cells did occur.

EXAMPLE 5

Expression of CIA-1 polypeptides

This embodiment illustrates that each of the CIA-1 ORFs 1–3, encoding a respective polynucleotide (herein referred to generally as CIA-1 polypeptide), can be inserted separately or together into various vectors including phage vectors and plasmids. Successful expression of the respective CIA-1 polypeptide, or peptide thereof containing an immunogenic epitope having one or more amino acid changes in CIA-1 (herein referred to as "peptide"), requires that either the insert comprising the gene (ORF) or gene fragment which encodes epitopes of the CIA-1 polypeptide, or the vector itself contain the necessary elements for transcription and translation which is compatible with, and recognized by the particular host system used for expression. DNA encoding the CIA-1 polypeptide or peptide, can be synthesized or isolated and sequenced using the methods and primer sequences as illustrated according to Example 1 herein. A variety of host systems may be utilized to express the CIA polypeptide or peptide, which include, but are not limited to bacteria transformed with a bacteriophage vector, plasmid vector, or cosmid DNA; yeast containing yeast vectors; fungi containing fungal vectors; insect cell lines infected with virus (e.g. baculovirus); avian cells transfected with plasmid or viral expression vectors, or infected with recombinant virus; and mammalian cell lines transfected with plasmid or viral expression vectors, or infected with recombinant virus (e.g. vaccinia virus, adenovirus, adeno-associated virus, retrovirus, etc.).

Using methods known in the art of molecular biology, including methods described above, various promoters and enhancers can be incorporated into the vector or the DNA sequence encoding CIA-1 polypeptide to increase the recombinant expression of the polypeptide, provided that the increased expression is compatible with (for example, non-toxic to) the particular host cell system used. Thus and importantly, the DNA sequence can consist of the gene encoding CIA-1 polypeptide, or any segment/fragment of the gene which encodes a functional epitope, and containing one or more amino acid changes in CIA-1, of the respective CIA-1 polypeptide. Further, the DNA can be fused to DNA encoding other antigens, such as other viral capsid proteins, or other bacterial, fungal, parasitic, or viral antigens to create a genetically fused (sharing a common peptide backbone) multivalent antigen for use as an improved vaccine composition.

The selection of the promoter will depend on the expression system used. Promoters vary in strength, i.e. ability to facilitate transcription. Generally, for the purpose of expressing a cloned gene, it is desirable to use a strong promoter in order to obtain a high level of transcription of the gene and expression into gene product. For example, bacterial, phage, or plasmid promoters known in the art from which a high level of transcription has been observed in a host cell system comprising *E. coli* include the lac promoter, trp promoter, recA promoter, ribosomal RNA promoter, the $P_R$ and $P_L$ promoters, lacUV5, ompF, bla, lpp, and the like, may be used to provide transcription of the inserted DNA sequence encoding E amino acid sequences. For insect cells, as host cells, the polyhedrin or p10 promoters of baculovirus can be used. For mammalian cells, as host cells, promoters such as the simian virus (SV40) early or late promoter, and the methallothionein-I (MT-I).

Additionally, if the CIA-1 polypeptide may be lethal or detrimental to the host cells, the host cell strain/line and expression vectors may be chosen such that the action of the promoter is inhibited until specifically induced. For example, in certain operons the addition of specific inducers is necessary for efficient transcription of the inserted DNA (e.g., the lac operon is induced by the addition of lactose or isopropylthio-beta-D-galactoside). A variety of operons such as the trp operon, are under different control mechanisms. The trp operon is induced when tryptophan is absent in the growth media. The $P_L$ promoter can be induced by an increase in temperature of host cells containing a temperature sensitive lambda repressor. In this way, greater than 95% of the promoter-directed transcription may be inhibited in uninduced cells. Thus, expression of recombinant CIA-1 polypeptide or peptides may be controlled by culturing transformed or transfected cells under conditions such that the promoter controlling the expression from the inserted DNA encoding CIA-1 polypeptide or peptide is not induced, and when the cells reach a suitable density in the growth medium, the promoter can be induced for expression from the inserted DNA.

Other control elements for efficient gene transcription or message translation include enhancers, and regulatory signals. Enhancer sequences are DNA elements that appear to increase transcriptional efficiency in a manner relatively independent of their position and orientation with respect to a nearby gene. Thus, depending on the host cell expression vector system used, an enhancer may be placed either upstream or downstream from the inserted DNA sequences encoding CIA-1 polypeptide to increase transcriptional efficiency. As illustrated previously in Example 1 herein, other specific regulatory sequences such as binding sites for various transcription factors have been identified which may effect the expression from the gene encoding CIA-1 polypeptide. These or other regulatory sites, such as transcription or translation initiation signals, can be used to regulate the expression of the gene encoding CIA-1 polypeptide, or gene fragments thereof. Such regulatory elements may be inserted into DNA sequences encoding CIA-1 polypeptide or nearby vector DNA sequences using recombinant DNA methods described herein for insertion of DNA sequences.

Accordingly, CIA-1 specific DNA sequences containing an ORF encoding for polypeptide, or a DNA fragment of the ORF encoding peptide, can be ligated into an expression vector at a specific site in relation to the vector's promoter, control, and regulatory elements so that when the recombinant vector is introduced into the host cell, the CIA-1 specific DNA sequences (e.g. ORF-1, or ORF-2, or ORF-3) can be expressed in the host cell. For example, the CIA-1 specific DNA sequences containing its own regulatory elements can be ligated into an expression vector in a relation or orientation to the vector promoter, and control elements which will allow for expression of CIA-1 polypeptide. The recombinant vector is then introduced into the appropriate host cells, and the host cells are selected, and screened for those cells containing the recombinant vector. Selection and screening may be accomplished by methods known in the art including detecting the expression of a marker gene (e.g., drug resistance marker) present in the plasmid, immuno-screening for production of CIA-1 polypeptide epitopes using antisera generated to CIA-1-specific epitopes, and probing the DNA of the host's cells for CIAV-specific nucleotide sequences using one or more oligonucleotides and methods described according to Example 1 herein, and by Soiné et al. (1993, supra).

Figure 2:
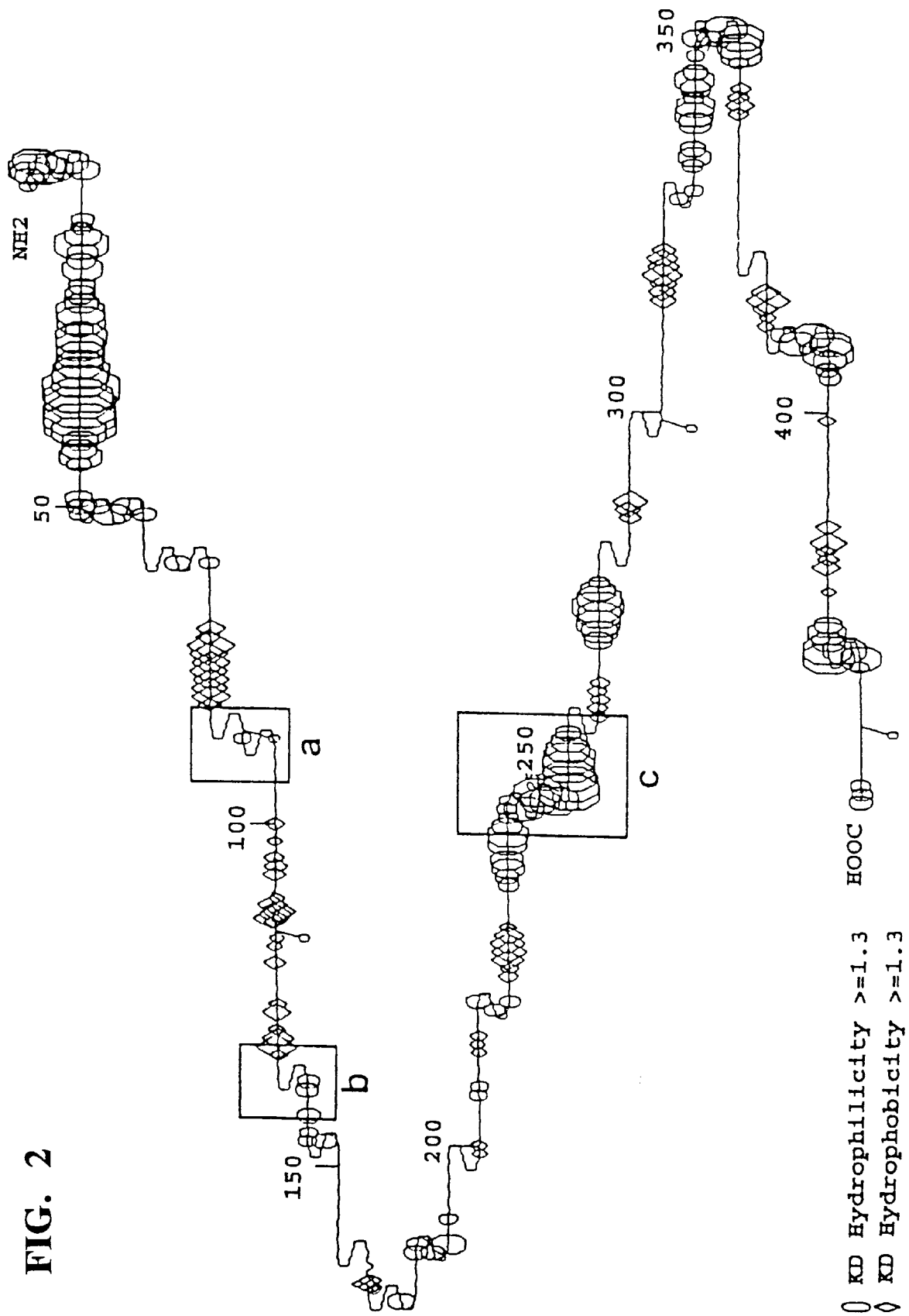

Genetic engineering techniques may also be used to characterize, modify and/or adapt the CIA-1 polypeptides encoded by ORFs 1–3. For example, site-directed mutagenesis to modify an polypeptide fragment in regions outside the immunogenic domains, may be desirable to increase the solubility of the subfragment to allow for easier purification. Further, genetic engineering techniques can be used to generate DNA sequences encoding a portion of the amino acid sequence of a CIA-1 polypeptide containing one or more amino acid changes in CIA-1. For example, from the sequences disclosed as SEQ ID NO:1–3, it can be determined which restriction enzyme or combination of restriction enzymes may be used to generate sequences encoding CIA-1 peptides. Restriction enzyme selection may be done so as not to destroy the immunopotency of the resultant peptide or oligopeptide. Antigenic sites of a protein may vary in size but can consist of from about 7 to about 14 amino acids. Thus, a polypeptide the size of any one of those encoded by CIA-1 ORFs 1–3 may contain many discrete antigenic sites; therefore, many partial gene sequences could encode antigenic epitopes of CIA-1 polypeptide that contain one or more amino acid changes of CIA-1. A hydrophilicity plot of CIA-1 ORF-1 is shown in FIG. 2. Consequently, using FIG. 1 and SEQ ID NO:1 as guide, restriction enzyme combinations may be used to generate DNA sequences, which when inserted into the appropriate vector, are capable of directing the production of CIA-1 ORF-1, ORF-2, or ORF-3-specific amino acid sequences (polypeptides or peptides) comprising up to one or more antigenic epitopes that contain one or more amino acid changes in CIA-1.

To further illustrate this embodiment, CIA-1 ORF-1, ORF-2 and ORF-3 may be separately cloned into a baculovirus vector. Each ORF may be subcloned into a transfer plasmid which includes a baculovirus polyhedrin promoter, multiple cloning sites, beta galactosidase under etl promoter. From the plasmid subclones described in Example 1, a XhoI-NotI restriction fragment of about 650 bp containing ORF-2 can be subcloned into compatible sites of the transfer plasmid. The resultant recombinant plasmid can be subsequently co-transfected with wild type Autographa Californica Nuclear Polyhedrosis Virus (AcMNPV) genomic DNA into the Fall Army Spodoptera Frugiperda cell line SF21 using a modified calcium phosphate precipitation technique for insect cells. Expressed recombinant virus plaques can then be identified in the infected insect cell monolayers by plaque assay and staining with X-gal. Construction of recombinant AcMNPV-ORF-3 can be done using similar methods. For example, a XhoI-NotI restriction fragment of about 365 bp containing ORF-3 may be subcloned into compatible sites of the transfer plasmid.

EXAMPLE 6

Purification of CIA-1 polypeptide or peptide

A CIA-1 polypeptide encoded by either ORF-1, ORF-2 or ORF-3, or a peptide containing an immunogenic epitope containing one or more amino acid changes in CIA-1 can be purified for use as an immunogen in vaccine formulations. Recombinant CIA-1 polypeptide or peptide produced from an expression vector system, can be purified with methods known in the art including detergent extraction, chromatography (e.g., ion exchange, affinity, immunoaffinity, or sizing columns), differential centrifugation, differential solubility, or other standard techniques for the purification of proteins. Immunopurification of the CIA-1 polypeptide from a host cell expression system preparation may be accomplished using methods known in the art for immunoaffinity chromatography. Monoclonal antibodies specific for epitopes of that polypeptide may be linked to a chromatographic matrix to form an affinity matrix. The preparation containing the polypeptide or peptide containing that epitope is then incubated with the affinity matrix allowing the antibodies to bind to the polypeptide or peptide. The affinity matrix is then washed to remove unbound components and the polypeptide or peptide is then eluted from the affinity matrix resulting in a purified preparation of polypeptide or peptide. Purified polypeptide may be chemically or enzymatically cleaved into peptides using methods known to those in the art. Alternatively, peptides of the CIA-1 polypeptide may be chemically synthesized using the respective deduced amino acid sequence shown in either SEQ ID NO:1–3. Oligopeptides are defined herein as a series of peptides corresponding to a portion of the amino acid sequence of either of the polypeptides disclosed in SEQ ID NO:1–3 that are synthesized as one or chemically-linked. Such peptides or oligopeptides can be synthesized using one of the several methods of peptide synthesis known in the art including standard solid peptide synthesis using tert-butyloxycarbonyl amino acids (Mitchell et al., 1978, *J. Org. Chem.* 43: 2845–2852), using 9-fluorenylmethyloxycarbonyl amino acids on a polyamide support (Dryland et al., 1986, *J. Chem. So. Perkin Trans.* I, 125–137); by pepscan synthesis (Geysen et al., 1987, *J. Immunol. Methods* 03: 259; 1984, *Proc. Natl. Acad. Sci. USA* 81: 3998); or by standard liquid phase peptide synthesis. Modification of the peptides or oligopeptides, such as by deletion and substitution of amino acids (and including extensions and additions to amino acids) and in other ways, may be made so as to not substantially detract from the immunological properties of the peptide or oligopeptide. In particular, the amino acid sequence of the CIA polypeptide may be altered by replacing one or more amino acids with functionally equivalent amino acids resulting in an alteration which is silent in terms of an observed difference in the physicochemical behavior of the protein, peptide, or oligopeptide.

EXAMPLE 7

Methods and compounds for vaccine formulations

This embodiment of the present invention is to provide CIA-1 polypeptide encoded by ORF-1 or ORF-2 or ORF-3 and/or peptides thereof, to be used in as immunogens in a prophylactic and/or therapeutic vaccine for active immunization to protect against or treat infections caused by CIAV. One or more polypeptides of CIA-1, because it is not a cell culture-adapted strain, may be advantageous as an antigen in a vaccine formulation. It has been noted that changes occur to CIAV strains during passage in culture (Meehan et al., 1992, *Arch. Virol.* 124: 301–319; Todd et al., 1995 *Avian Pathol.* 24: 171–188). In the field of virology, it has been observed that neutralization by antibodies can differ substantially between primary viral isolates and viral strains adapted to cell culture (Mascola et al., 1994, *J. Infect. Dis.* 169: 48–54). Thus, in some cases, vaccine antigens made from primary isolates may be more effective in inducing a protective response to viral strains encountered by animals. A preferred embodiment is a vaccine comprised of both CIA-1 VP1 and VP1. For vaccine development, the CIA-1-specific amino acid sequences comprising the immunogen may be purified from a host containing a recombinant vector which expresses CIA-1 polypeptide, or peptide. Such hosts include, but are not limited to, bacterial transformants, yeast transformants, filamentous fungal transformants, and cultured cells that have been either infected or transfected with a vector which encodes CIA-1-specific amino acid sequences. Peptides or oligopeptides corresponding to portions of the CIA-1 polypeptide and containing one or more amino acid changes in CIA-1 may be produced from chemical or enzymatic cleavage of the respective CIA-1 polypeptide, or chemically synthesized using methods known in the art and with the amino acid sequence deduced from the nucleotide sequence of the respective CIA-1 ORF as a reference. Alternatively, the peptides or oligopeptides may be produced from a recombinant vector. In either case, the CIA-1 polypeptide, peptide or oligopeptide immunogen is included as the relevant immunogenic material in the vaccine formulation, and in therapeutically effective amounts, to induce an immune response. Many methods are known for the introduction of a vaccine formulation into the animal to be vaccinated. These include, but are not limited to, intradermal, intramuscular, intraperitoneal, intravenous, subcutaneous, ocular, intranasal, and oral administration. The vaccine may further comprise a physiological carrier such as a solution, a polymer or liposomes; and an adjuvant, or a combination thereof.

Various adjuvants are used in conjunction with vaccine formulations. The adjuvants aid in attaining a more durable and higher level of immunity using smaller amounts of vaccine antigen or fewer doses than if the vaccine antigen were administered alone. The mechanism of adjuvant action is complex and not completely understood. However, it may involve immunomodulation through the stimulation of cytokine production, phagocytosis and other activities of the reticuloendothelial system, as well as delayed release and degradation/processing of the antigen to enhance immune recognition. Examples of adjuvants include incomplete Freund's adjuvant, Adjuvant 65 (containing peanut oil, mannide monooleate and aluminum monostearate), oil emulsions, Ribi adjuvant, the pluronic polyols, polyamines, Avridine, Quil A, saponin, MPL, QS-21, and mineral gels such as aluminum hydroxide, aluminum phosphate, etc.

Another embodiment of this mode of the invention involves the production of CIA-1-specific amino acid sequences as a hapten, i.e. a molecule which cannot by itself elicit an immune response. In such case, the hapten may be covalently bound to a carrier or other immunogenic molecule which will confer immunogenicity to the coupled hapten when exposed to the immune system. Thus, such a CIA-1-specific hapten linked to a carrier molecule may be the immunogen in a vaccine formulation.

Another mode of this embodiment provides for either a live recombinant viral vaccine, recombinant bacterial vaccine, recombinant attenuated bacterial vaccine, or an inactivated recombinant viral vaccine which is used to protect against infections caused by CIAV. The recombinant microorganism (bacteria or virus) used for the vaccine may comprise a viral vector containing the CIA-1 ORF under the control of a strong promoter so that the respective polypeptide is expressed. Examples of such viral vectors known in the art include a nononcogenic Marek's disease virus (MDV), live attenuated infectious laryngotracheitis virus, attenuated chick fowlpox virus, or attenuated herpes virus of turkey; i.e. an infectious virus that can be engineered to express vaccine antigens derived from other organisms. Alternatively, the microorganism may consist of attenuated Salmonella strains (Stocker et al., U.S. Pat. Nos. 5,210,035; 4,837,151; and 4,735,801; and Curtiss et al., 1988, *Vaccine* 6: 155–160). The recombinant live microorganism, which is attenuated or otherwise treated so that it does not cause disease by itself, is used to immunize chicks or chickens. Subsequent replication of the recombinant microorganism within the host provides a continual stimulation of the immune system with vaccine antigens comprising epitopes of the CIA-1 polypeptide, thereby providing long-lasting immunity. When the immune response is protective against subsequent CIAV infection, the live vaccine itself may be used in a preventative vaccine against CIAV. Further, protective antibodies may be vertically transmitted to offspring.

To illustrate this mode of the embodiment, using molecular biological techniques such as those illustrated in Examples 1 and 3, either CIA-1 ORF-1, ORF-2 or ORF-3, or a combination thereof, may be inserted into the viral vector genomic DNA at a site which allows for expression of the respective polypeptide epitopes (i.e., is operatively linked to one or more regulatory sequences necessary for expression) but does not negatively affect the growth or replication of the viral vector. The resultant recombinant virus can be used as the immunogen in a vaccine formulation. The same methods can be used to construct an inactivated recombinant viral vaccine formulation except that the recombinant virus is inactivated, such as by chemical means known in the art, prior to use as an immunogen.

Additionally, one or more recombinant CIA-1 polypeptides could be one of multiple antigens in a combined vaccine against chicken infectious anemia and against other diseases of poultry. Examples of such antigens useful in a combined vaccine, and their corresponding pathogen and disease caused, are known in the art of veterinary medicine. For example, the combined vaccine may include genes encoding antigens of infectious laryngotracheitis virus causing infectious laryngotracheitis; one or more copies of the gene encoding the viral hemagglutinin glycoprotein of the chicken fowlpox virus causing fowlpox; one or more copies of either or both of the gene encoding the HN antigen or the gene encoding the F antigen of Newcastle disease virus causing Newcastle disease; and one or more copies of a gene encoding either glycoprotein B (gB), L1 or A4 of Marek's disease virus.

In another variation of this embodiment, using methods known to those skilled in the art, either of CIA-1 ORF-1–3 sequences, or a combination thereof, can be inserted into any virus vector useful as a vaccine, wherein transcription of the ORF is under the control of a constitutive promoter. This recombinant viral vaccine vector can either be inoculated into embryos in ovo or into chicks directly after hatching. In yet another variation of this embodiment, using methods known to those skilled in the art, the ORF sequence is inserted into a plasmid vector. The plasmid vector is constructed to have an origin of replication such as from VS40, and a eukaryotic promoter or transcriptional control elements such as the CIAV promoter-enhancer, MDV promoter, or other viral transcriptional control elements known in the art, which is operatively-linked to the ORF sequence. The recombinant plasmid is constructed such that in vivo transcription of the ORF is regulated by either an inducible promoter or a constitutive promoter. The recombinant plasmid is then injected into embryos in ovo or into chicks directly after hatching. Direct gene transfer into animals resulting in expression of the exogenous gene in vascular endothelial cells, as well as the tissue of the major organs, has been demonstrated by techniques in the art such as by injecting intravenously an expression plasmid:cationic liposome complex (Zhu et al., 1993, *Science* 261: 209–211). Other effective methods for delivering vector DNA into a target cell are known in the art. In one example, purified recombinant plasmid DNA containing viral genes has been used to inoculate (whether parentally, mucosally, or via gene-gun immunization) chickens to induce a protective immune response (Fynan et al., 1993, *Proc. Natl. Acad. Sci. USA* 90: 11478–11482). The nucleic acid molecule (recombinant plasmid or viral vector) can be administered in a pharmaceutically acceptable carrier or diluent and may contain compounds that can enhance the effectiveness of the vaccine. These additional compounds include, but are not limited to, adjuvants that modulate and enhance the immune response, or other compounds which increase the uptake of nucleic acid by the cells.

In another example, cells removed from the chick or embryo can be transfected or electroporated by standard procedures known in the art, resulting in the introduction of the vector DNA into the target cell. Cells containing the vector DNA may be selected from those lacking the vector DNA by incorporating a selection marker into the vector such as the neo gene, and growing the cells in the corresponding selection media such as in the presence of G418. Selected cells, containing the recombinant expression vector for expressing the CIA-1 ORF transcripts, may then be reintroduced into the chick or embryo.

Another variation of this embodiment involves the development of transgenic chickens which express polypeptide encoded by one or more CIA-1 ORFs, wherein the production of the polypeptide is under the control of an inducible promoter or a constitutive promoter. Methods known in the art for producing a transgenic chicken include the introduction of the genetic material into the chicken germ line cells by microinjection, viral infection, or embryonic stem cell transfer. Introduction of the genetic material, such as a sequence which can be transcribed and translated into CIA-1 polypeptide, results in lineages that carry the integrated genetic material. Detection of transgenics can be accomplished by isolating tissue cells and examining the isolated cells for integration of the transgene by Southern blot analysis, or for expression of the CIA-1 ORF into polypeptide by immunofluorescence of isolated tissue.

It should be understood that while the invention has been described in detail herein, the examples were for illustrative purposes only. Other modifications of the embodiments of the present invention that are obvious to those skilled in the art of molecular biology, veterinary medicine, and related disciplines are intended to be within the scope of the appended claims.

What is claimed is:

1. A vaccine formulation comprising an immunologically effective amount of at least one chicken infectious anemia virus polypeptide selected from the group consisting of SEQ ID NO:1, or SEQ ID NO:1 in combination with SEQ ID NO:2.

2. The vaccine formulation according to claim 1, in which the at least one polypeptide was produced recombinantly from a host cell system genetically engineered to include an expression vector containing a nucleotide sequence selected from the group consisting:
   (a) ORF-1 as shown in SEQ ID NO:1;
   (b) ORF-2 as shown in SEQ ID NO:2;
   (c) a combination of (a), and (b);
wherein said host cell is selected from the group consisting of bacteria, yeast, filamentous fungi, insect cell lines, avian cells, and mammalian cell lines.

3. The vaccine formulation according to claim 1, further comprising a pharmaceutical carrier.

4. The vaccine according to claim 1, further comprising a recombinant vector containing a nucleotide sequence, wherein the nucleotide sequence encodes said at least one polypeptide, and is operatively linked to an expression control element; and wherein the vector is selected from the group consisting of a viral vector and a plasmid.

5. The vaccine according to claim 4, wherein the viral vector comprises a live attenuated virus selected from the group consisting of Marek's disease virus, infectious laryngotracheitis virus, chicken fowlpox virus, and herpesvirus of turkey.

6. The vaccine formulation according to claim 4, wherein the vaccine is a combined vaccine and further comprises one or more nucleotide sequences operatively linked to an expression control element and encoding one or more antigens useful against a viral disease of poultry other than chicken infectious anemia, wherein said viral disease is selected from the group consisting of infectious laryngotracheitis, chicken fowlpox, Newcastle disease, and Marek's disease.

7. The vaccine formulation according to claim 3, wherein the vaccine is a combined vaccine and further comprises one or more nucleotide sequences operatively linked to an expression control element and encoding one or more antigens useful against a viral disease of poultry other than chicken infectious anemia, wherein said viral disease is selected from the group consisting of infectious laryngotracheitis, chicken fowlpox, Newcastle disease, and Marek's disease.

8. A method of immunizing poultry against chicken infectious anemia virus comprising administering a prophylactically effective amount of the vaccine formulation according to claim 1.

9. A method of immunizing poultry against chicken infectious anemia virus comprising administering a prophylactically effective amount of the vaccine formulation according to claim 2.

10. A method of immunizing poultry against chicken infectious anemia virus comprising administering a prophylactically effective amount of the vaccine formulation according to claim 3.

11. A method of immunizing poultry against chicken infectious anemia virus comprising administering a prophylactically effective amount of the vaccine formulation according to claim 4.

12. A method of immunizing poultry against chicken infectious anemia virus comprising administering a prophylactically effective amount of the vaccine formulation according to claim 7.

* * * * *

UNITED STATES PATENT AND TRADEMARK OFFICE
CERTIFICATE OF CORRECTION

PATENT NO. : 5,965,139
DATED : Oct. 12, 1999
INVENTOR(S) : Schat et al.

It is certified that error appears in the above-identified patent and that said Letters Patent is hereby corrected as shown below:

Col. 30, line 56 - "claim 3" should be ---claim 5---.

Signed and Sealed this

Ninth Day of May, 2000

Attest:

Q. TODD DICKINSON

Attesting Officer          Director of Patents and Trademarks

SEQUENCE LISTING

```
(1) GENERAL INFORMATION:

(iii) NUMBER OF SEQUENCES: 7

(2) INFORMATION FOR SEQ ID NO:1 :

(i) SEQUENCE CHARACTERISTICS:
          (A) LENGTH:  2298 nucleotides
          (B) TYPE: nucleic acid
          (C) STRANDEDNESS: double-stranded
          (D) TOPOLOGY: linear (ii) MOLECULE TYPE: genomic DNA (iii) HYPOTHETICAL: yes (vi) ORIGINAL SOURCE:
          (A) ORGANISM: Chicken infectious anemia virus
          (B) STRAIN: CIA-1
          (C) CELL TYPE: virus (v) SEQUENCE DESCRIPTION: SEQ ID NO:1 :

GAATTCCGAG TGGTTACTAT TCCATCACCA TTCTAGCCTG TACACAGAAA    50

GTCAAGATGG ACGAATCGCT CGACTTCGCT CGCGATTCGT CGAAGGCGGG   100

GGGCCGGAGG CCCCCCGGTG GCCCCCCTCC AACGAGTGGA GCATGTACAG   150

GGGGGTACGT CATCCGTACA GGGGGGTACG TCACAAAGAG GCGTTCCCGT   200

ACAGGGGGGT ACGTCACGCG TACAGGGGGG TACGTCACAG CCAATCAGAA   250

GCTGCCACGT TGCGAAAGTG ACGTTTCGAA AATGGGCGGC GCAAGCCTCT   300

CTATATATTG AGCGCACATA CCGGTCGGCA GTAGGTATAC GCAAGGCGGT   350

CCGGGTGGAT GCACGGGAAC GGCGGACAAC CGGCCGCTGG GGGCAGTGAA   400

TCGGCGCTTA GCCGAGAGGG GCAACCTGAG CCCAGCGGAG CCGCGCAGGG   450

GCAAGTAATT TCAAATGAAC GCTCTCCAAG AAGATACTCC ACCCGGACCA   500

TCAACGGTGT TCAGGCCACC AACAAGTTCA CGGCCGTTGG AAACCCCTCA   550

CTGCAGAGAG ATCCGGATTG GTATCGCTGG AATTACAATC ACTCTATCGC   600

TGTGTGGCTG CGGGAATGCT CGCGCTCCCA CGCTAAGATC TGCAACTGCG   650

GACAATTCAG AAAGCACTGG TTTCAAGAAT GTGCCGGACT TGAGGACCGA   700

TCAACCCAAG CCTCCCTCGA AGAAGCGATC CTGCGACCCC TCCGAGTACA   750

GGGTAAGCGA GCTAAAAGAA AGCTTGATTA CCACTACTCC CAGCCGACCC   800
```

-continued

```
CGAACCGCAA GAAGGTGTAT AAGACTGTAA G ATG GCA AGA CGA GCT    846
                                  Met Ala Arg Arg Ala
                                   1               5

CGC AGA CCG AGA GGC CGA TTT TAC TCC TTC AGA AGA GGA CGG    888
Arg Arg Pro Arg Gly Arg Phe Tyr Ser Phe Arg Arg Gly Arg
             10                  15

TGG CAC AAC CTC AAG CGA CTT CGA CGA AGA TAT AAA TTT CGA    930
Trp His Asn Leu Lys Arg Leu Arg Arg Arg Tyr Lys Phe Arg
 20              25                  30

CAT CGG AGG AGA CAG CGG TAT CGT AGA CGA GCT TTT AGG AAG    972
His Arg Arg Arg Gln Arg Tyr Arg Arg Arg Ala Phe Arg Lys
 35              40                  45

GCC TTT CAC AAC CCC CGC CCC GGT ACG TAT AGT GTG AGG CTG   1014
Ala Phe His Asn Pro Arg Pro Gly Thr Tyr Ser Val Arg Leu
         50                  55                  60

CCG AAC CCC CAA TCT ACT ATG ACT ATC CGC TTC CAA GGA ATC   1056
Pro Asn Pro Gln Ser Thr Met Thr Ile Arg Phe Gln Gly Ile
             65                  70                  75

ATA TTT CTC ACG GAA GGA CTC ATT CTG CCT AAA AAC AGC ACA   1098
Ile Phe Leu Thr Glu Gly Leu Ile Leu Pro Lys Asn Ser Thr
                 80                  85

GCG GGG GGC TAT GCA GAC CAC TTG TAC GGG GCG AGA GTC GCC   1140
Ala Gly Gly Tyr Ala Asp His Leu Tyr Gly Ala Arg Val Ala
 90                  95                 100

AAG ATC TCT GTG AAC CTG AAA GAG TTC CTG CTA GCG TCA ATG   1182
Lys Ile Ser Val Asn Leu Lys Glu Phe Leu Leu Ala Ser Met
    105                 110                 115

AAC CTG ACA TAC GTG AGC AAA ATC GGA GGC CCC ATC GCC GGT   1224
Asn Leu Thr Tyr Val Ser Lys Ile Gly Gly Pro Ile Ala Gly
        120                 125                 130

GAG TTG ATT GCG GAC GGG TCT CAA TCA CAA GCC GCG CAG AAC   1266
Glu Leu Ile Ala Asp Gly Ser Gln Ser Gln Ala Ala Gln Asn
            135                 140                 145

TGG CCT AAT TGC TGG CTG CCG CTA GAT AAT AAC GTG CCC TCC   1308
Trp Pro Asn Cys Trp Leu Pro Leu Asp Asn Asn Val Pro Ser
                150                 155

GCG ACA CCA TCG GCA TGG TGG AGA TGG GCC TTA ATG ATG ATG   1350
Ala Thr Pro Ser Ala Trp Trp Arg Trp Ala Leu Met Met Met
160                 165                 170

CAG CCC ACG GAC TCT TGC CGG TTC TTT AAC CAC CCT AAG CAG   1392
Gln Pro Thr Asp Ser Cys Arg Phe Phe Asn His Pro Lys Gln
    175                 180                 185

ATG ACC CTG CAA GAC ATG GGT CGC ATG TTT GGG GGC TGG CAC   1434
Met Thr Leu Gln Asp Met Gly Arg Met Phe Gly Gly Trp His
        190                 195                 200

CTG TTC CGA CAC ATT GAA ACC CGC TTT CAG CTC CTT GCC ACT   1476
Leu Phe Arg His Ile Glu Thr Arg Phe Gln Leu Leu Ala Thr
            205                 210                 215

AAG AAT GAG GGA TCC TTC AGC CCC GTG GCG AGT CTT CTC TCC   1518
Lys Asn Glu Gly Ser Phe Ser Pro Val Ala Ser Leu Leu Ser
                220                 225

CAG GGA GAG TAC CTC ACG CGT CGG GAC GAT GTT AAG TAC AGC   1560
Gln Gly Glu Tyr Leu Thr Arg Arg Asp Asp Val Lys Tyr Ser
230                 235                 240

AGC GAT CAC CAG AAC CGG TGG CGA AAA GGC GGA CAA CCG ATG   1602
Ser Asp His Gln Asn Arg Trp Arg Lys Gly Gly Gln Pro Met
    245                 250                 255

ACG GGG GGT ATT GCT TAT GCG ACC GGG AAA ATG AGA CCC GAC   1644
Thr Gly Gly Ile Ala Tyr Ala Thr Gly Lys Met Arg Pro Asp
        260                 265                 270
```

```
GAG CAA CAG TAC CCT GCT ATG CCC CCA GAC CCC CCG ATC ATC   1686
Glu Gln Gln Tyr Pro Ala Met Pro Pro Asp Pro Pro Ile Ile
            275                 280                 285

ACC GCT ACT ACA GCG CAA GGC ACG CAA GTC CGC TGC ATG AAT   1728
Thr Ala Thr Thr Ala Gln Gly Thr Gln Val Arg Cys Met Asn
                290                 295

AGC ACG CAA GCT TGG TGG TCA TGG GAC ACA TAC ATG AGC TTT   1770
Ser Thr Gln Ala Trp Trp Ser Trp Asp Thr Tyr Met Ser Phe
300                 305                 310

GCA ACA CTC ACA GCA CTC GGT GCA CAA TGG TCT TTT CCT CCA   1812
Ala Thr Leu Thr Ala Leu Gly Ala Gln Trp Ser Phe Pro Pro
        315                 320                 325

GGG CAA CGT TCA GTT TCT AGA CGG TCC TTC AAT CAC CAC AAG   1854
Gly Gln Arg Ser Val Ser Arg Arg Ser Phe Asn His His Lys
            330                 335                 340

GCG AGA GGA GCC GGA GAC CCC AAA GGG CAG AGA TGG CAC ACG   1896
Ala Arg Gly Arg Gly Asp Pro Lys Gly Gln Arg Tyr His Thr
                345                 350                 355

CTG GTG CCG CTA GGC ACG GAG ACC ATC ACG GAC AGC TAC ATG   1938
Leu Val Pro Leu Gly Thr Glu Thr Ile Thr Asp Ser Tyr Met
                    360                 365

AGT GCA CCT GCA TCA GAG CTG GAC ACG AAT TTC TTT ACG CTT   1980
Ser Ala Pro Ala Ser Glu Leu Asp Thr Asn Phe Phe Thr Leu
370                 375                 380

TAC GTA GCG CAA GGC ACA AAT AAG TCG CAG CAG TAC AAG TTC   2022
Tyr Val Ala Gln Gly Thr Asn Lys Ser Gln Gln Tyr Lys Phe
        385                 390                 395

GGC ACA GCT ACA TAC GCG CTA AAG GAG CCG GTA ATG AAG AGC   2064
Gly Thr Ala Thr Tyr Ala Leu Lys Glu Pro Val Met Lys Ser
            400                 405                 410

GAT GCA TGG GCA GTG GTA CGC GTC CAG TCG GTC TGG CAA CTG   2106
Asp Ala Trp Ala Val Val Arg Val Gln Ser Val Trp Gln Leu
                415                 420                 425

GGT AAC AGG CAG AGG CCA TAC CCA TGG GAC GTC AAC TGG GCG   2148
Gly Asn Arg Gln Arg Pro Tyr Pro Trp Asp Val Asn Trp Ala
                    430                 435

AAC AGC ACC ATG TAC TGG GGG ACG CAG CCC TG AAAAGGGGGG    2190
Asn Ser Thr Met Tyr Trp Gly Thr Gln Pro
440                 445         449

GGGGCTAAAG CCCCCCCCCC TTGAACCCCC CCCTGGGGGG GATTCCCCCC   2240

CAGACCCCCC CTTTAAATAG CACTCAATAA ACGCAGCAAA TAGATTTATC   2290

GCACTATC                                                 2298

(2) INFORMATION FOR SEQ ID NO:2 :

(i) SEQUENCE CHARACTERISTICS:
        (A) LENGTH:   648 nucleotides
        (B) TYPE: nucleic acid
        (C) STRANDEDNESS: double-stranded
        (D) TOPOLOGY: linear (ii) MOLECULE TYPE: genomic DNA (iii) HYPOTHETICAL: yes (vi) ORIGINAL SOURCE:
        (A) ORGANISM: Chicken infectious anemia virus
        (B) STRAIN: CIA-1
        (C) CELL TYPE: virus (v) SEQUENCE DESCRIPTION: SEQ ID NO:2 :
```

```
ATG CAC GGG AAC GGC GGA CAA CCG GCC GCT GGG GGC AGT GAA        42
Met His Gly Asn Gly Gly Gln Pro Ala Ala Gly Gly Ser Glu
 1               5                  10

TCG GCG CTT AGC CGA GAG GGG CAA CCT GGG CCC AGC GGA GCC        84
Ser Ala Leu Ser Arg Glu Gly Gln Pro Gly Pro Ser Gly Ala
15                  20                  25

GCG CAG GGG CAA GTA ATT TCA AAT GAA CGC TCT CCA AGA AGA       126
Ala Gln Gly Gln Val Ile Ser Asn Glu Arg Ser Pro Arg Arg
        30                  35                  40

TAC TCC ACC CGG ACC ATC AAC GGT GTT CAG GCC ACC AAC AAG       168
Tyr Ser Thr Arg Thr Ile Asn Gly Val Gln Ala Thr Asn Lys
            45                  50                  55

TTC ACG GCC GTT GGA AAC CCC TCA CTG CAG AGA GAT CCG GAT       210
Phe Thr Ala Val Gly Asn Pro Ser Leu Gln Arg Asp Pro Asp
                60                  65                  70

TGG TAT CGC TGG AAT TAC AAT CAC TCT ATC GCT GTG TGG CTG       252
Trp Tyr Arg Trp Asn Tyr Asn His Ser Ile Ala Val Trp Leu
                    75                  80

CGG GAA TGC TCG CGC TCC CAC GCT AAG ATC TGC AAC TGC GGA       294
Arg Glu Cys Ser Arg Ser His Ala Lys Ile Cys Asn Cys Gly
85                  90                  95

CAA TTC AGA AAG CAC TGG TTT CAA GAA TGT GCC GGA CTT GAG       336
Gln Phe Arg Lys His Trp Phe Gln Glu Cys Ala Gly Leu Glu
        100                 105                 110

GAC CGA TCA ACC CAA GCC TCC CTC GAA GAA GCG ATC CTG CGA       378
Asp Arg Ser Thr Gln Ala Ser Leu Glu Glu Ala Ile Leu Arg
            115                 120                 125

CCC CTC CGA GTA CAG GGT AAG CGA GCT AAA AGA AAG CTT GAT       420
Pro Leu Arg Val Gln Gly Lys Arg Ala Lys Arg Lys Leu Asp
130                 135                 140

TAC CAC TAC TCC CAG CCG ACC CCG AAC CGC AAG AAG GTG TAT       462
Tyr His Tyr Ser Gln Pro Thr Pro Asn Arg Lys Lys Val Tyr
                    145                 150

AAG ACT GTA AGA TGG CAA GAC GAG CTC GCA GAC CGA GAG GCC       504
Lys Thr Val Arg Trp Gln Asp Glu Leu Ala Asp Arg Glu Ala
155                 160                 165

GAT TTT ACG CCT TCA GAA GAG GAC GGT GGC ACA ACC TCA AGC       546
Asp Phe Thr Pro Ser Glu Glu Asp Gly Gly Thr Thr Ser Ser
        170                 175                 180

GAC TTC GAC GAA GAT ATA AAT TTC GAC ATC GGA GGA GAC AGC       588
Asp Phe Asp Glu Asp Ile Asn Phe Asp Ile Gly Gly Asp Ser
            185                 190                 195

GGT ATC GTA GAC GAG CTT TTA GGA AGG CCT TTC ACA ACC CCC       630
Gly Ile Val Asp Glu Leu Leu Gly Arg Pro Phe Thr Thr Pro
                200                 205                 210

GCC CCG GTA CGT ATA GTG                                       648
Ala Pro Val Arg Ile Val
                    215
```

(2) INFORMATION FOR SEQ ID NO:3 :

(i) SEQUENCE CHARACTERISTICS:
        (A) LENGTH:   363 nucleotides
        (B) TYPE: nucleic acid
        (C) STRANDEDNESS: double-stranded
        (D) TOPOLOGY: linear (ii) MOLECULE TYPE: genomic DNA (iii) HYPOTHETICAL: yes (vi) ORIGINAL SOURCE:
        (A) ORGANISM: Chicken infectious anemia virus
        (B) STRAIN: CIA-1

(C) CELL TYPE: virus (v) SEQUENCE DESCRIPTION: SEQ ID NO:3 :

```
ATG AAC GCT CTC CAA GAA GAT ACT CCA CCC GGA CCA TCA ACG      42
Met Asn Ala Leu Gln Glu Asp Thr Pro Pro Gly Pro Ser Thr
 1               5                  10

GTG TTC AGG CCA CCA ACA AGT TCA CGG CCG TTG GAA ACC CCT      84
Val Phe Arg Pro Pro Thr Ser Ser Arg Pro Leu Glu Thr Pro
15                  20                  25

CAC TGC AGA GAG ATC CGG ATT GGT ATC GCT GGA ATT ACA ATC     126
His Cys Arg Glu Ile Arg Ile Gly Ile Ala Gly Ile Thr Ile
        30                  35                  40

ACT CTA TCG CTG TGT GGC TGC GCG AAT GCT CGC GCT CCC ACG     168
Thr Leu Ser Leu Cys Gly Cys Ala Asn Ala Arg Ala Pro Thr
            45                  50                  55

CTA AGA TCT GCA ACT GCG GAC AAT TCA GAA AGC ACT GGT TTC     210
Leu Arg Ser Ala Thr Ala Asp Asn Ser Glu Ser Thr Gly Phe
                60                  65                  70

AAG AAT GTG CCG GAC TTG AGG ACC GAT CAA CCC AAG CCT CCC     252
Lys Asn Val Pro Asp Leu Arg Thr Asp Gln Pro Lys Pro Pro
                    75                  80

TCG AAG AAG CGA TCC TGC GAC CCC TCC GAG TAC AGG GTA AGC     294
Ser Lys Lys Arg Ser Cys Asp Pro Ser Glu Tyr Arg Val Ser
 85                 90                  95

GAG CTA AAA GAA AGC TTG ATT ACC ACT ACT CCC AGC CGA CCC     336
Glu Leu Lys Glu Ser Leu Ile Thr Thr Thr Pro Ser Arg Pro
    100                 105                 110

CGA ACC GCA AAA AGG CGT ATA AGA CTG                         363
Arg Thr Ala Lys Arg Arg Ile Arg Leu
            115                 120
```

(2) INFORMATION FOR SEQ ID NO:4 :

(i) SEQUENCE CHARACTERISTICS:
        (A) LENGTH: 25 nucleotides
        (B) TYPE: nucleic acid
        (C) STRANDEDNESS: single-stranded
        (D) TOPOLOGY: linear (ii) MOLECULE TYPE: DNA (vi) ORIGINAL SOURCE:
        (A) ORGANISM: Chicken infectious anemia virus
        (B) STRAIN: CIA-1
        (C) CELL TYPE: virus (vii) IMMEDIATE SOURCE: synthesized (v) SEQUENCE DESCRIPTION: SEQ ID NO:4 :

ATCGAATTCG AGTGGTTACT ATTCC                                  25

(2) INFORMATION FOR SEQ ID NO:5 :

(i) SEQUENCE CHARACTERISTICS:
        (A) LENGTH: 24 nucleotides
        (B) TYPE: nucleic acid
        (C) STRANDEDNESS: single-stranded
        (D) TOPOLOGY: linear (ii) MOLECULE TYPE: DNA (vi) ORIGINAL SOURCE:
        (A) ORGANISM: Chicken infectious anemia virus
        (B) STRAIN: CIA-1
        (C) CELL TYPE: virus (vii) IMMEDIATE SOURCE: synthesized -continued

```
    (v) SEQUENCE DESCRIPTION: SEQ ID NO:5 :

CGGTGATTCT TACTCCCTAG GAAG                                              24

(2) INFORMATION FOR SEQ ID NO:6 :

(i) SEQUENCE CHARACTERISTICS:
        (A) LENGTH: 24 nucleotides
        (B) TYPE: nucleic acid
        (C) STRANDEDNESS: single-stranded
        (D) TOPOLOGY: linear (ii) MOLECULE TYPE: DNA (vi) ORIGINAL SOURCE:
        (A) ORGANISM: Chicken infectious anemia virus
        (B) STRAIN: CIA-1
        (C) CELL TYPE: virus (vii) IMMEDIATE SOURCE: synthesized (v) SEQUENCE DESCRIPTION: SEQ ID NO:6 :

GAGGGATCCT TCAGCCCCGT GGCG                                              24

(2) INFORMATION FOR SEQ ID NO:7 :

(i) SEQUENCE CHARACTERISTICS:
        (A) LENGTH: 25 nucleotides
        (B) TYPE: nucleic acid
        (C) STRANDEDNESS: single-stranded
        (D) TOPOLOGY: linear (ii) MOLECULE TYPE: DNA (vi) ORIGINAL SOURCE:
        (A) ORGANISM: Chicken infectious anemia virus
        (B) STRAIN: CIA-1
        (C) CELL TYPE: virus (vii) IMMEDIATE SOURCE: synthesized (v) SEQUENCE DESCRIPTION: SEQ ID NO:7 :

TCGGAATTCG ATAGTGCGAT AAATC                                             25
```